United States Patent [19]
Simpkins et al.

[11] Patent Number: 5,859,001
[45] Date of Patent: Jan. 12, 1999

[54] NEUROPROTECTIVE EFFECTS OF POLYCYCLIC PHENOLIC COMPOUNDS

[75] Inventors: James W Simpkins, Gainesville, Fla.; Katherine Gordon, Winchester, Mass.; Pattie S. Green, Gainesville, Fla.

[73] Assignees: University of Florida Research Foundation, Inc., Gainesville, Fla.; Apollo Genetics, Cambridge, Mass.

[21] Appl. No.: 685,574

[22] Filed: Jul. 24, 1996

Related U.S. Application Data

[60] Provisional application No. 60/001,394 Jul. 24, 1995.
[51] Int. Cl.⁶ .................................................. A61K 31/56
[52] U.S. Cl. ............................................. 514/182
[58] Field of Search ............................................. 514/182

[56] References Cited

FOREIGN PATENT DOCUMENTS

| | | |
|---|---|---|
| 0 339 579 | 11/1989 | European Pat. Off. . |
| 0 606 661 | 7/1994 | European Pat. Off. . |
| 0 659 418 | 6/1995 | European Pat. Off. . |
| 28 03 582 | 8/1979 | Germany . |
| WO87/02666 | 5/1987 | WIPO . |
| WO92/03049 | 3/1992 | WIPO . |
| WO92/07855 | 5/1992 | WIPO . |
| WO95/13076 | 5/1995 | WIPO . |

OTHER PUBLICATIONS

Chemical Abstracts, vol. 96, No. 7, Feb. 15, 1982; abstract No. 46388, Waefelaer, "Structural Analogs of Apomorhine".

*Primary Examiner*—William R.A. Jarvis
*Attorney, Agent, or Firm*—Bromberg & Sunstein LLP

[57] ABSTRACT

This application relates to the use of non-estrogen compounds having a terminal phenol group in a four-ring cyclopentanophenanthrene compound structure for conferring neuroprotection to cells and for the treatment of neurodegenerative diseases.

8 Claims, 13 Drawing Sheets

| | NAME | % OF 17β-ESTRADIOL NEUROPROTECTION |
|---|---|---|
| R=H | 3,17β-ESTRADIOL | 100 |
| R=CH₃ | 3,17β-ESTRADIOL 3-O-ME | −1.5 |
| R=H | ESTRATRIENE-3-ol | 103 |
| R=H | 3,17α-ESTRADIOL | 81 |
| R=CH₃CO | 3,17α-ESTRADIOL 3-ACETATE | −20 |
| R=H | 2-HYDROXY-17β-ESTRADIOL | 70 |
| R=CH₃ | 17β-ESTRADIOL 2,3-O-ME | 7 |
| R=H | ESTRONE | 58 |
| R=CH₃ | ESTRONE 3-O-ME | −11 |
| R=H | ESTRIOL | 46 |
| R=CH₃ | ESTRIOL 3-O-ME | 2 |
| R=H | ETHYNYL ESTRADIOL | 41 |
| R=CH₃ | MESTRANOL | −6 |

FIG.13

| NAME | % OF 17β-ESTRADIOL NEUROPROTECTION |
|---|---|
| 3,17β-ESTRADIOL | 100 |
| PHENOL | −27 |
| DIETHYLSTILBESTEROL | 74 |
| DIETHYLSTILBESTEROL-MONO-O-ME | 60 |
| DIETHYLSTILBESTEROL-di-O-ME | 2 |

FIG.14

| TREATMENT | LIVE CELL NUMBER ± SEM ($10^3$ CELLS/ml) |
|---|---|
| SERUM FREE CONTROLS | 203 ± 16 |
| BUTYLATED HYDROXYANISOL | 182 ± 16 |
| BUTYLATED HYDROXYTOLUENE | 175 ± 11 |

FIG.15

NEUROPROTECTIVE EFFECTS OF POLYCYCLIC PHENOLIC COMPOUNDS

CROSS REFERENCE

This application claims the benefit of the earlier filing date of U.S. provisional patent application Ser. No. 60/001,394, filed Jul. 24, 1995.

TECHNICAL FIELD

The present invention relates to compositions and methods for protecting cells in the central nervous system of subjects from cell death and for stimulating neuronal survival in subjects with neurodegenerative conditions.

BACKGROUND

Pathological conditions resulting from the accelerated or ongoing death of neurons are prevalent in today's society and include chronic diseases such as Alzheimer's disease and Parkinson's disease, acute diseases such as stroke, brain cell loss that follows myocardial infarction, and acute neuronal injury associated with spinal cord trauma and head trauma. Chronic and acute neurodegenerative diseases and acute neuronal injury as well as associated mortality and morbidity are largely untreatable. The consequences of patient disability resulting from these conditions is a high cost to society of patient care as well as a significant reduction in quality of life. Effective therapeutic approaches directed to the prevention or reduction of neuron death or damage associated with the above conditions are needed. At present, the greatest challenge in the development of therapeutic agents for treating conditions in the brain resulting from neuron loss include obtaining an efficacious drug that is relatively non-toxic, suitable for use in both females and males, and which can readily access the brain across the blood-brain barrier.

Estrogen compounds have been found to protect neurons from cell death and have utility in retarding the progression of neurodegenerative diseases such as Alzheimer's disease. (Simpkins et al. WO 95/12402, Behl et al. (1995) Biochem. Biophys. Res. Commun. 216: 473–482;: Bishop et al. (1994) Molecular and Cellular Neuroscience 5:303–308; Simpkins et al. (1994) Neurobiology of Aging 15:s195–s197). Furthermore, Simpkins et al. WO 95/12402 has shown that alpha isomers of estrogen compounds, previously thought to be biologically inert, are effective in retarding neurodegeneration. This demonstration provided for the first time an opportunity to administer estrogen therapeutically to men without associated sex-related side effects.

The mechanisms by which estrogen compounds bring about a neuroprotective effect are unknown although these compounds have been shown to have a number of different physiological and biochemical effects on neurons. For example, estrogen has been shown to stimulate the production of neurotrophic agents that in turn stimulate neuronal growth. (REF) Estrogen compounds have also been found to inhibit NMDA-induced cell death in primary neuronal cultures (Bahl et al. Biochem. Biophys Res. Commun. (1995) 216:973; Goodman et al. J. Neurochem (1996) 66:1836), and further to be capable of removing oxygen free radicals and inhibiting lipid peroxidation. (Droescher et al. WO 95/13076). However, the potential effect of free radicals on neurons per se is unproven. Droescher et al. describes a cell free 'in vitro' assay systems using lipid peroxidation as an endpoint in which several estrogens as well as vitamin E were shown to have activity. Estradiol has also been reported to reduce lipid peroxidation of membranes (Niki (1987) Chem. Phys. Lipids 44:227; Nakano et al. Biochem. Biophys. Res. Comm. (1987) 142:919; Hall et al. J. Cer. Blood Flow Metab. (1991)11:292. Other compounds including certain 21-amino steroids and a glucocorticosteroid have been found to act as anti-oxidants and have been examined for their use in spinal cord injury as well as head trauma, ischemia, and stroke. (Wilson et al. (1995) J. Trauma 39:473; Levitt et al. (1994) J. Cardiovasc. Pharmacol 23:136; Akhter et al. (1994) Stroke 25; 418).

As described above, a number of factors may be involved in neuroprotection. Therapeutic agents that are selected on the basis of a single biochemical mechanism may have limited generalized utility in treating disease or trauma in patients. For example, in order to achieve an anti-oxidant effect in vitro using estrogen, Droescher et al. used very high doses of estrogens. Such doses, even if effective on neurons in vivo, would have limited utility in treating chronic neurological conditions because of associated problems of toxicity that result from prolonged use of high dosages.

It would be beneficial to identify a class of compounds that are non-sex related and have demonstrated biological efficacy in protecting neurons from cell death, where such compounds could be used in the treatment of the chronic as well as the acute conditions caused by neurodegenerative diseases, trauma, and aging at non-toxic dosages. An understanding of the structural requirements for compositions capable of inducing neuroprotection would provide the basis for designing novel drugs that have enhanced neuroprotective properties while at the same time having reduced adverse side effects.

SUMMARY OF THE INVENTION

The present invention satisfies the above stated need for a class of compounds that is effective in protecting neurons from deterioration and cell death arising from disease, trauma or aging and may be used to achieve a similar effect in male and female subjects with minimal adverse side effects.

In a preferred embodiment of the invention, a method is provided for conferring neuroprotection on a population of cells in a subject, having the steps of providing a non-estrogen compound, having a terminal phenol group in a structure containing at least a second ring having a molecular weight that is less than 1000 Daltons; and administering the compound in an effective dose to the population of cells to confer neuroprotection.

In another embodiment of the invention, a method of treating a neurodegenerative condition in a subject is provided, which includes the steps of selecting an effective dose of a compound having a terminal phenol ring having a molecular weight less than 1000D and at least one additional ring structure covalently linked to the phenol ring; and administering the compound to the subject.

In another embodiment of the invention, the compound used in the method may have a four-ring structure, a three-ring structure or a two-ring structure where the four-ring structure may be administered at an effective dose that achieves a plasma concentration of less than 500 nM. The molecular weight of the compound may be greater than 170 D.

In another embodiment of the invention, the three ring structure is a phenanthrene compound which may further be selected from the group consisting of tetrahydrophenanthrene and a octahydrophenanthrene more particularly a phenanthrenemethanol or a phenanthrencarboxyaldehyde.

In another embodiment of the invention, the two-ring structure may be fused and include a naphthol and naphthalene or may be a non-fused two ring structure having a linkage group.

In an embodiment of the invention, the terminal phenol ring includes non-steroidal compounds. Embodiments of the invention utilize a compound having a phenolic A ring.

In a further embodiment of the invention, the dosage of the neuroprotective compound results in a plasma concentration of less than 500 nM, more particularly in the range of .02m nM–500 nM and more particularly in the range of 0.1 nM–1 nM.

BRIEF DESCRIPTION OF THE DRAWINGS

These and other features of the invention will be better understood with reference to the following description, appended claims, and accompanying drawings where

FIG. 13 is a table showing phenolic A ring requirement for the neuroprotectivity of estratrienes.

FIG. 14 is a table showing the neuroprotectivity of estradiol, phenol, and dipenols.

FIG. 15 is a table showing the effects of branched chain substituted phenols on SK-N-SH live cell numbers at 48 hours exposure.

DETAILED DESCRIPTION OF SPECIFIC EMBODIMENTS

Figure 1:
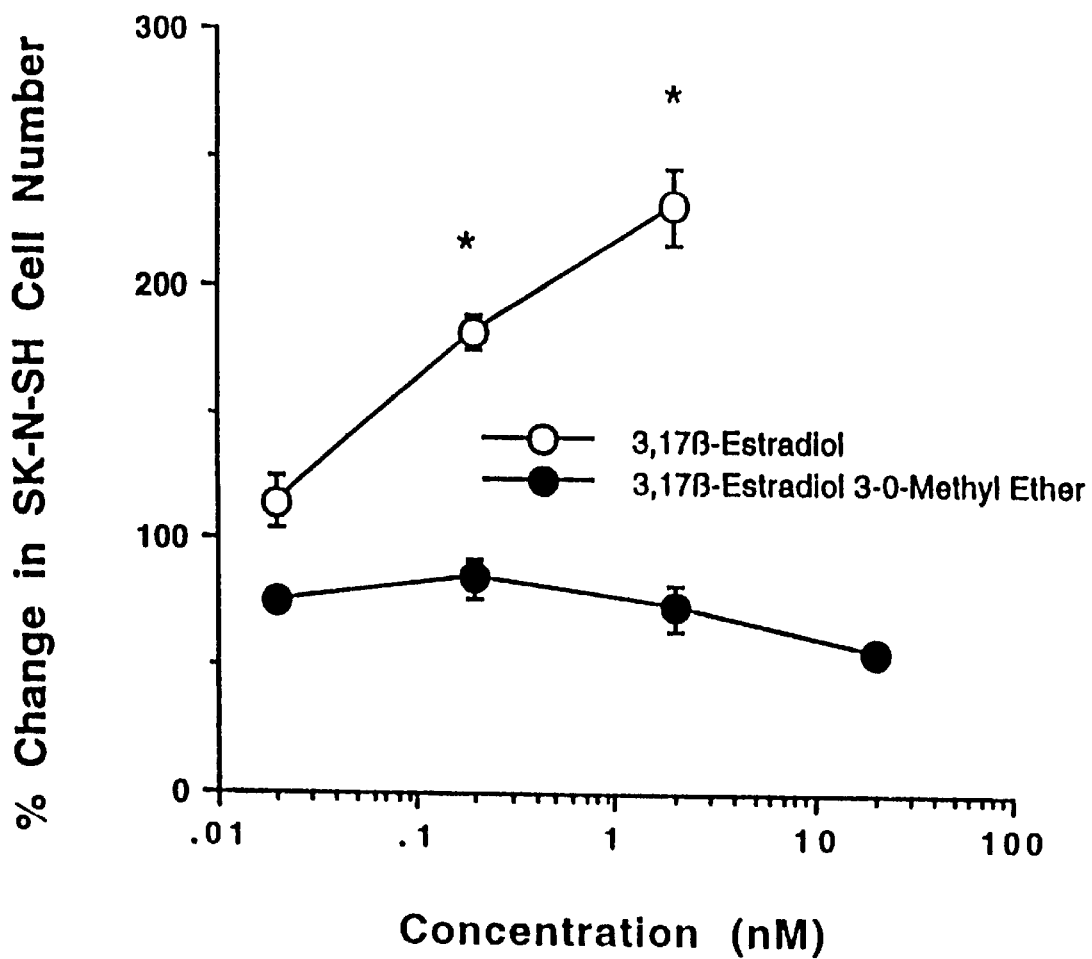
FIG. 1 shows the effects of 3,17β-estradiol and 3,17β-estradiol 3-O-methyl ether on the % change in live SK-N-SH cell number at 48 hours of serum deprivation. Raw data were compared to the respective serum-free control group by analysis of variance and Scheffe's F test and data were then normalized to the serum free group (=100%). *=p<0.05 versus serum-free controls. Data are expressed as mean±SEM for 6 wells per group.

Neuroprotection is defined here and in the claims as the inhibition of progressive deterioration of neurons that leads to cell death.

A non-estrogen compound is defined here and in the claims as a compound, other than an estrogen compound, described in the 11 th Edition of "Steroids" from Steraloids Inc., Wilton, N.H.

A phenol ring is referred to as "terminal" here and in the claims, when it is the ultimate carbon ring on a molecule consisting of more than 1 carbon ring.

A steroid is defined here and in the claims as a compound having numbered carbon atoms arranged in a 4-ring structure (J. American Chemical Society 82:5525–5581 (1960) and Pure and Applied Chemistry 31: 285–322 (1972)).

"Neurodegenerative disorder" is defined here and in the claims as a disorder in which progressive loss of neurons occurs either in the peripheral nervous system or in the central nervous system. Examples of neurodegenerative disorders include: chronic neurodegenerative diseases such as Alzheimer's disease, Parkinson's disease, Huntington's chorea, diabetic peripheral neuropathy, multiple sclerosis, amyotrophic lateral sclerosis; aging; and acute neurodegenerative disorders including: stroke, traumatic brain injury, schizophrenia, peripheral nerve damage, hypoglycemia, spinal cord injury, epilepsy, and anoxia and hypoxia.

These examples are not meant to be comprehensive but serve merely as an illustration of the term "neurodegenerative disorder."

The present invention identifies a method of neuroprotection that utilizes a novel class of neuroprotective compounds, where the class of compounds is identified according to a set of features that has here been recognized for the first time as determinative of neuroprotection. This method is further suited for the treatment of neurodegenerative diseases, trauma and aging in human subjects.

The protection of neurons from severe degeneration is an important aspect of treatment for patients with acute or chronic neurodegenerative disorders, an example of chronic disease being Alzheimer's disease. For Alzheimer's patients, the method of the invention may be of significant therapeutic use. Other diseases for which such a method may be effective include Parkinson's disease, Huntington's disease, AIDS Dementia, Wernicke-Korsakoff's related dementia (alcohol induced dementia), age related dementia, age associated memory impairment, brain cell loss due to any of the following; head trauma, stroke, hypoglycemia, ischemia, anoxia, hypoxia, cerebral edema, arteriosclerosis, hematoma and epilepsy; spinal cord cell loss due to any of the conditions listed under brain cell loss; and peripheral neuropathy. Because of the observed cytoprotective properties, it is suggested that one pathway of action for the polycyclic phenolic compounds is the inhibition of apoptosis.

The characteristic set of features that define the class of neuroprotective compounds include (a) the presence of two or more ring structures in the compound where the compound has a size range less than 1000 Daltons; (b) a terminal phenol ring and (c) an effective dose in vivo for causing a neuroprotective effect.

Figure 11:
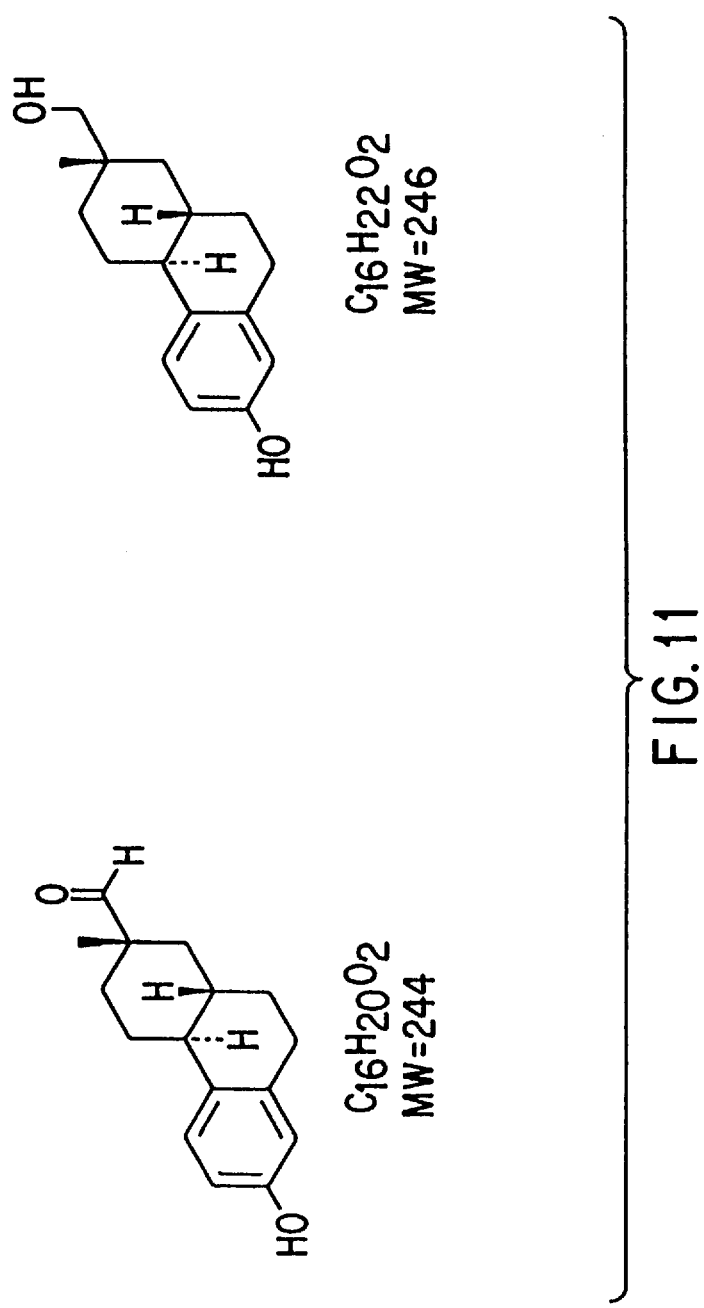
FIG. 11 shows the structures of 3-ring compounds: [2S-(2a ,4a α,10a α)]-1,2,3,4,4a,9,10,10a -octahydro-7-hydroxy-2-methyl-2-phenanthrenemethanol (PAM) and [2S-(2a ,4a α,10a β)]-1,2,3,4,4a,9,10,10a -octahydro-7-hydroxy-2-methyl-2-phenanthrenecarboxaldehyde (PACA).
Figure 12:
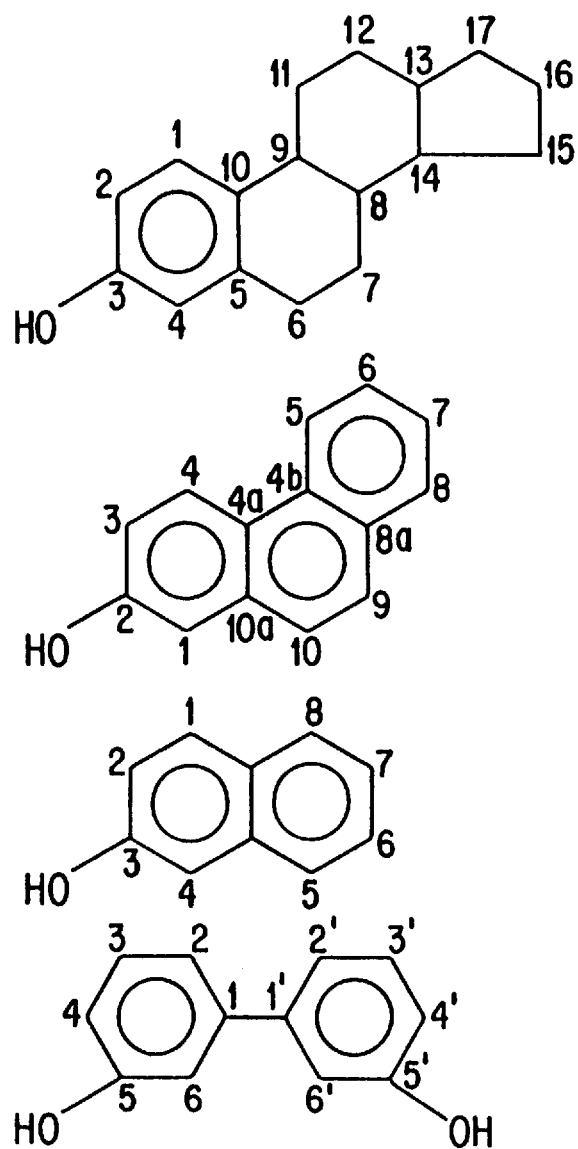
FIG. 12 shows the generalized core ring structures with numbered carbons (a) 4-ring structure, (b) 3-ring structure, (c) 2-ring structure (fused) (d) 2 ring structure (non-fused).

The class of neuroprotective compounds described here includes (a) compounds that are characterized by two-carbon rings (FIG. 14); (b) compounds that are characterized by three-carbon rings (FIG. 11, 12); and steroids that are characterized by 4-carbon rings, (FIG. 12). Neuroprotective compounds may further comprise 5-carbon rings or more providing that the overall molecular weight of 1000 Daltons is not exceeded.

According to the invention, an assay has been used as disclosed in Example 1, that utilizes SK-N-SH neuronal cells under stress to determine neuroprotection by test compounds. 3,17β-estradiol has been selected as the control, because of its previously demonstrated neuroprotective effects (Simpkins WO 95/12402). The neuroprotective activity of the control compound is shown in FIG. 1. It can be seen from FIG. 1, that at 48 hrs of serum deprivation, the percentage of live SK-N-SH cells increases by 100% in the presence of 2 nM 3,17β-estradiol.

This invention teaches that neuroprotection can be achieved at an effective dose providing low plasma concentrations of polycyclic phenolic compounds. More specifically, a neuroprotective effect can be achieved at plasma concentrations of less than 500 nM and more particularly between 0.1 nM and 1 nM. The relatively low effective dose of neuroprotective compounds capable of causing a neuroprotective effect according to the invention, is in stark contrast with the findings of others who have tested estrogens in in vitro assays. For example, Droescher et al. describe an $IC_{50}$ of 12.8 $\mu$M estrogen to inhibit free radical oxidation in a lipid peroxidation assay. The indirect lipid peroxidation assay for cell protection used by Droescher et al. is a biochemical assay and is not comparable to the neuron cell assay used in the invention to directly measure a cellular response. Consequently, the two assays cannot be directly compared and the results of one assay cannot be extrapolated to the other. The advantage of the neuroprotection assay used here is that live and dying cells are utilized to determine neuroprotection directly.

Figure 8:
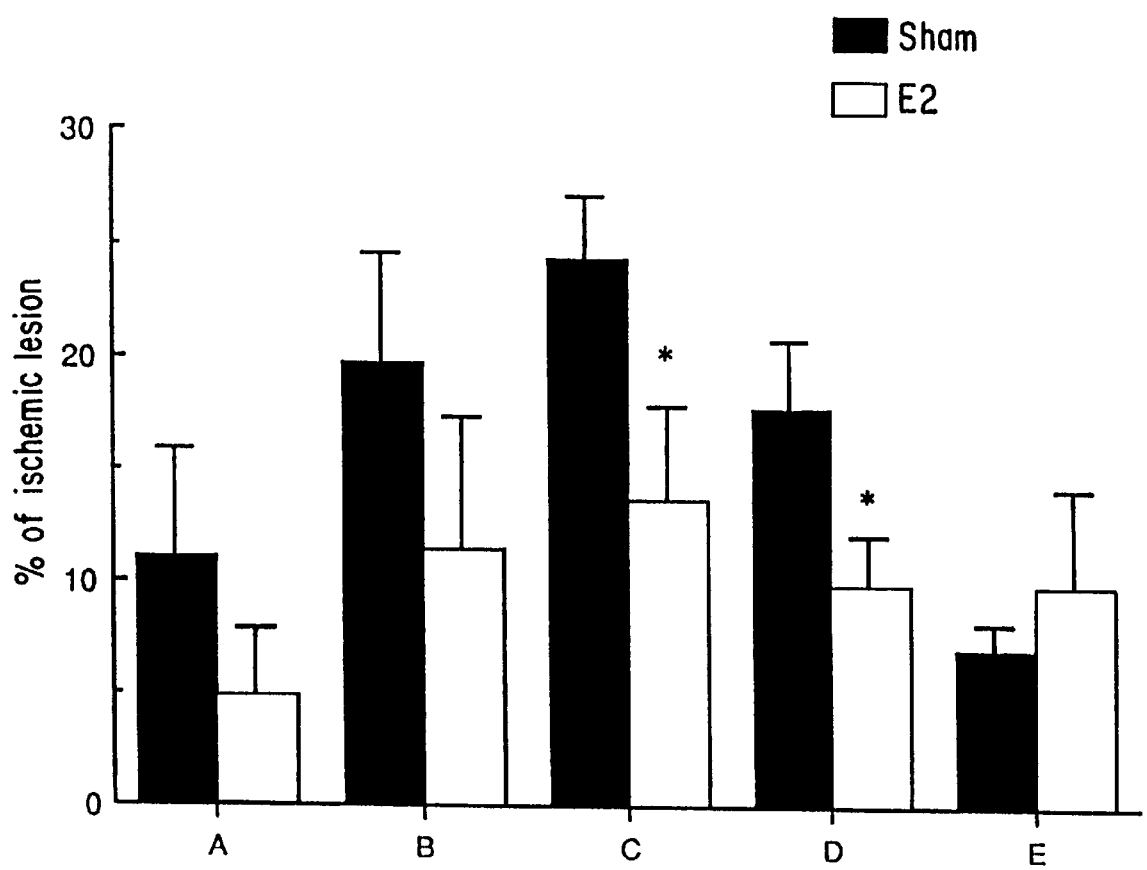
FIG. 8 shows the effect of treatment of ovariectomized rats with sham injection (oil) or with 3,17β-estradiol at 100 μg/kg body weight by subcutaneous injection, at 2 hours before occlusion of the middle cerebral artery. The maximum lesion size in brain cross sections of sacrificed animals was recorded and is shown as % of the cross sectional area of the brain. A,B,C,D and E correspond to brain sections at 7,9,11,13, and 15 mm respectively posterior to the olfactory bulb.

It is desirable that the amount of a neuroprotective agent to be used to treat a subject, should be within the range that is relatively non-toxic to the patient especially when the compound is used long-term. According to the invention, significant neuroprotection has been obtained in neuronal cell cultures at concentrations of 2 nM (FIGS. 1–6) and furthermore, significant neuroprotection has been achieved in rats at 100 μg/kg body weight. (a dose of compound at 100 μg/kg body weight provides approximately 0.4 nM–2 nM plasma concentration of the compound. (FIG. 8).

Figure 9:
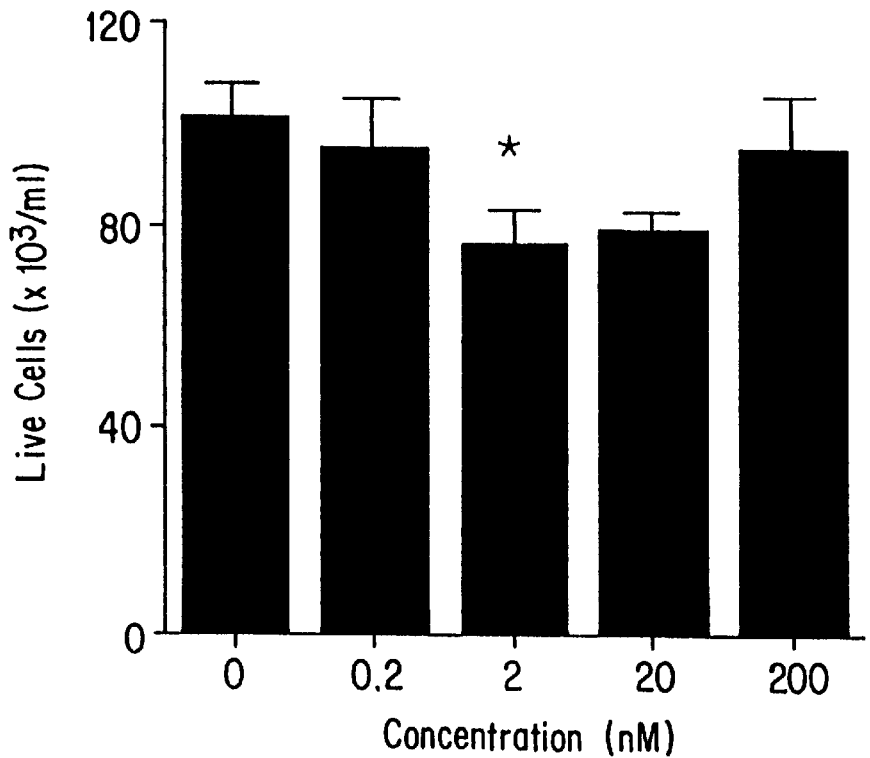
FIG. 9 shows the effects of progesterone at 2 nM on SK-N-SH live cell number at 48 hours of serum deprivation. Data are expressed as mean±SEM for 6 wells/group.
Figure 10:
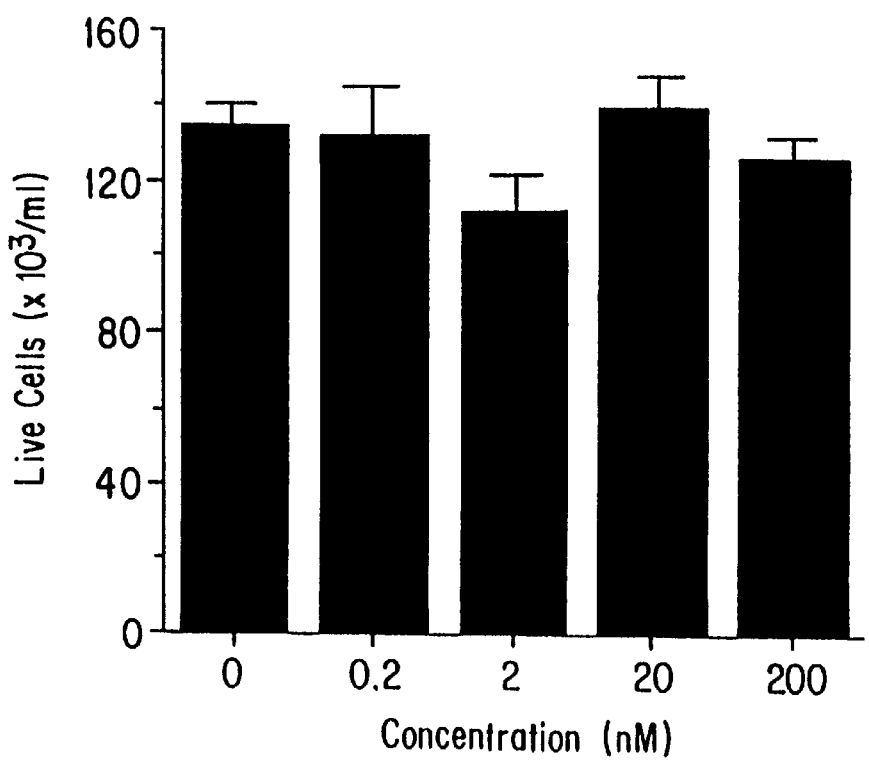
FIG. 10 shows the effects of corticosterone at 2 nM on SK-N-SH live cell number at 48 hours of serum deprivation. Data are expressed as mean±SEM for 6 wells/group.

According to the neuronal cell assay described in Example 1, it has been here demonstrated that the hydroxyl group on the phenolic A ring is required for neuroprotection. Following replacement of the hydroxyl group on the terminal phenol group with, for example, a methyl group, a significant loss of neuroprotective properties of the compound was observed (FIG. 1–6, FIGS. 13 and 14). Furthermore, compounds that normally lack a hydroxyl group on the terminal carbon ring, such as progesterone and corticosterone, show little or no neuroprotection (FIGS. 9 and 10). Applicants have further determined that the hydroxyl group on the terminal phenolic group may be located on any available carbon in order that neuroprotection to be maintained.

Figure 4:
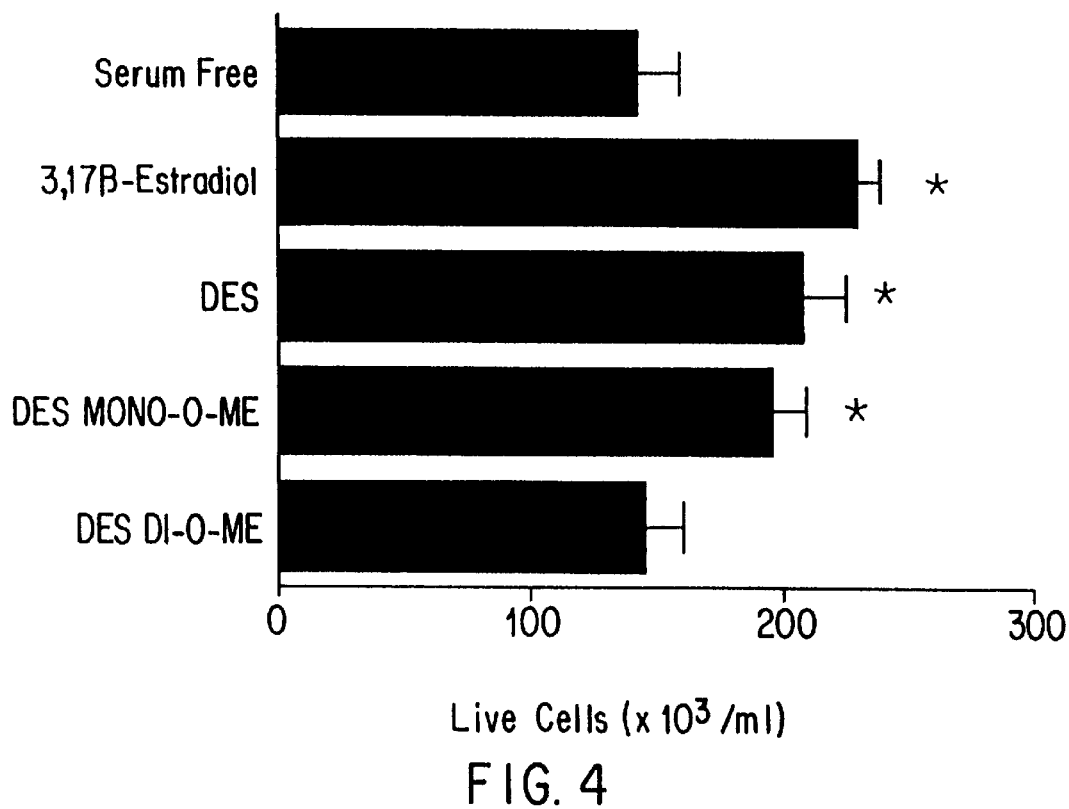
FIG. 4 shows the effects of 3,17β-estradiol, diethylstilbestrol (DES), DES mono-O-methyl ether (DES mono-O-ME) and DES di-O-methyl ether(DES Di-O-ME) all at a concentration of 2 nM, on live SK-N-SH cell number at 48 hours of serum deprivation. *=p<0.05 versus serum free controls and DES di-O-methyl ether groups. Data are expressed as mean±SEM for 6 wells/group.

It has been determined that neuroprotective compounds for use in the method of the invention require a terminal phenolic ring. These compounds may have an R group substitution on any suitable carbon on the terminal phenolic ring other then the carbon bearing the hydroxyl group and these R groups may be present in α or β isomeric configurations. Furthermore, phenol on its own is not neuroprotective nor are straight chain substitution of phenolic compounds (FIG. 15). However, a compound having a terminal phenolic ring and at least one other carbon ring is neuroprotective. For example, the non-fused two- ring structure, diethylstilbestrol, has demonstrated neuroprotective properties according to the invention (FIG. 14, FIG. 4). This compound has a terminal phenolic ring structure that is associated with a second phenolic ring via a linkage group. Removal of the hydroxyl group on the terminal phenolic ring results in a loss of neuroprotective activity.

Furthermore, compounds that are non-steroidal and have a terminal phenolic ring and at least two additional carbon ring structures include three-ring compounds (FIGS. 11, 12) such as exemplified by [2S-(2a ,4aα,10αβ) ]-1,2,3,4,4a,9,10,10a -octahydro-7hydroxy-2-methyl-2-phenanthrenemethanol (PAM) and [2S-(2a ,4aα,10 αβ) ]-1,2,3,4,4a,9,10,10a -octahydro-7hydroxy-2-methyl-2-phenanthrenecarboxyaldehyde (PACA) have been demonstrated to have a neuroprotective effect (see FIG. 5 and 6, 6a and 6b). The structure of these compounds are shown in FIG. 12. Two namomolar concentrations of either PAM or PACA were found to permit an increase in neuron cell survival of about 15%. Compounds having a terminal phenolic ring and at least three additional carbon rings have been shown to have a neuroprotective effect as exemplified by 3, 17β-estradiol. (FIG. 1). The upper size limit of a compound of the invention that is neuroprotective and has a terminal phenolic ring depends not so much on the number of carbon rings in the structure but rather whether the compound is of a sufficiently small size to permit crossing of the blood brain barrier.

The recommended route of administration of the neuroprotective compound includes oral, intramuscular, transdermal, buccal, intravenous and subcutaneous. Methods of administering the compound of the invention may be by dose or by controlled release vehicles.

The preferred embodiment of the invention includes a compound having a terminal phenolic ring and at least a second carbon ring. In addition to these required structures, the compound may have a number of R groups attached to any available site on the phenolic ring or elsewhere providing that the phenolic structure of the terminal ring is maintained. These R-groups may be selected from inorganic or organic atoms or molecules. Below, examples of a number of different types of R groups have been provided although the invention is not limited by these examples.

(a) The R group may include any inorganic R group including any of a halogen, an amide, a sulfate, a nitrate, fluoro, chloro, or bromo groups. Additionally, R groups selected from sodium, potassium and/or ammonium salts may be attached to the alpha or beta positions to replace hydrogen on any available carbon in the structure. The R-group may be organic or may include a mixture of organic molecules and ions. Organic R groups may include alkanes, alkenes or alkynes containing up to six carbons in a linear or branched array. For example, additional R group substituents may include methyl, ethyl, propyl, butyl, pentyl, hexyl, heptyl, dimethyl, isobutyl, isopentyl, tert-butyl, sec-butyl, isobutyl, methylpentyl, neopentyl, isohexyl, hexenyl, hexadiene, 1,3-hexadiene-5-yne, vinyl, allyl, isopropenyl, ethynyl, ethylidine, vinylidine, isopropylidene; methylene, sulfate, mercapto, methylthio, ethylthio, propylthio, methylsulfinyl, methylsulfonyl, thiohexanyl, thiobenyl, thiopenol, thiocyanato, sulfoethylamide, thionitrosyl, thiophosphoryl, p-toluenesulfonate, amino, imino, cyano, carbamoyl, acetamido, hydroxyamino, nitroso, nitro, cyanato, selecyanato, arccosine, pyridinium, hydrazide, semicarbazone, carboxymethylamide, oxime, hydrazone, sulfurtrimethylammonium, semicarbazone, o-carboxymethyloxime, aldehyde hemiacetate, methylether, ethylether, propylether, butylether, benzylether, methylcarbonate, carboxylate, acetate, chloroacetate, trimethylacetate, cyclopentylpropionate, propionate, phenylpropionate, carboxylic acid methylether, formate, benzoate, butyrate, caprylate, cinnamate, decylate, heptylate, enanthate, glucosiduronate, succinate, hemisuccinate, palmitate, nonanoate, stearate, tosylate, valerate, valproate, decanoate, hexahydrobenzoate, laurate, myristate, phthalate, hydroxyl, ethyleneketal, diethyleneketal, formate, chloroformate, formyl, dichloroacetate, keto, difluoroacetate, ethoxycarbonyl, trichloroformate, hydroxymethylene, epoxy, peroxy, dimethyl ketal, acetonide, cyclohexyl, benzyl, phenyl, diphenyl, benzylidene, and cyclopropyl groups. R groups may be attached to any of the constituent rings to form a pyridine, pyriazine, pyrimidine, or v-triazine. Additional R group substituents may include any of the six member or five member rings itemized in section b below.

(b) Any compound having in addition to the phenol A ring, a heterocyclic carbon ring which may be an aromatic or non-aromatic phenolic ring with any of the substitutions described in (a) above and further may be selected from for example, one or more of the following structures—phenanthrene, naphthalene, napthols, diphenyl, benzene, cyclohexane, 1,2-pyran, 1,4-Pyran, 1,2-pyrone, 1,4-pyrone, 1,2-dioxin, 1,3-dioxin (dihydro form), pyridine, pyridazine, pyrimidine, pyrazine, piperazine, s-triazine, as- triazine, v-triazine, 1,2,4-oxazine, 1,3,2-oxazine, 1,3,6-oxazine (pentoxazole), 1,2,6 oxazine, 1,4-oxazine, o-isoxazine, p-isoxazine, 1,2,5-oxathiazine, 1,2,6-oxathiazine, 1,4,2-oxadiazine, 1,3,5,2-oxadiazine, morpholine (tetrahydro-p-isoxazine), any of the six ringed structure listed above being a terminal group in the compound. Additionally, any of the above carbon ring structure may be linked directly or via a linkage group to any further heterocyclic aromatic or non aromatic carbon ring including: furan; thiophene (thiofuran); pyrrole (azole); isopyrrole (isoazole); 3-isopyrrole (isoazole); pyrazole (1,2-daizole); 2-isoimidazole (1,3-isodiazole); 1,2,3-triazle; 1,2,4 triazole; 1,2-diothiole; 1,2,3-oxathiole, isoxazole (furo(a) monozole); oxazole (furo(b) monazole); thiazole; isothiazole; 1,2,3-oxadiazole; 1,2,4-oxadiazole, 1,2,5-oxadiazole, 1,3,5 oxadiazole, 1,2,3,4-oxatiazole; 1,2,3,5-oxatriazole; 1,2,3-dioxazole; 1,2,4-dioxazole; 1,3,2-dioxazole; 1,3,4-dioxazole; 1,2,5-oxathiazole; 1,3-oxathiole, cyclopentane. These compounds in turn may have associated R groups selected from section (a) or section (b) above that are substituted on the carbon ring at any of the available sites.

(c) Any compound including those listed above, that may form a cyclopentanophen(a)anthrene ring compound and which, for example may be selected from the group consisting of 1,3,5(10), 6,8-estrapentaene, 1,3,5(10), 6,8,11-estrapentaene, 1,3,5 (10)6,8,15-estrapentaene, 1,3,5(10), 6,-estratetraene, 1,3,5(10), 7-estratetraene, 1,3,5(10)8-estratetraene, 1,3,5(10)16-estratetraene, 1,3,5(10)15-estratetraene, 1,3,5(10)- estratriene, 1,3,5(10) 15- estratriene.

(d) Any compound including precursors or derivatives selected from raloxifen, tamoxifen, androgenic compounds, and their salts where an intact phenol ring is present with a hydroxyl group present on carbons 1,2,3 and 4 of the terminal phenol ring.

(e) Any compound in the form of a prodrug, that may be metabolized to form an active polycyclic phenolic compound having neuroprotective activity.

Administration of any of the compounds of the invention may include the use of a single compound or a mixture of neuroprotective compounds.

Example 1: Assay to Identify Neuroprotective Compounds

The cell line, SK-N-SH, a well characterized human neuroblastoma cell line, was used to test potential neuroprotective drugs. This cell line is widely considered representative of neuronal cells and an appropriate assay system for evaluation of pharmaceutical neuroprotective drugs for human diseases and injury.

SK-N-SH cells were obtained from American Type Tissue Collection (Rockville, Md.). Cell cultures were grown to confluency in RPMI-1640 media supplemented with 10% Fetal Bovine Serum (FBS), 100 U/ml penicillin G, and 100 mg/ml streptomycin at 37° C. and under 5% $CO_2$ and 95% air. Media was changed three times weekly; SK-N-SH cells were backcultured every five to seven days to maintain cell lines and cells used in the following experiments were in passages seven to twelve. The growth media were initially decanted and the cells were rinsed with 0.02% EDTA that was subsequently discarded. Another aliquot of 0.02% EDTA was then added and after a 30 min incubation of 37° C., the cells were counted on a Neubauer hemacytometer (Fisher Scientific Inc., Orlando, Fla.) and resuspended in appropriate media. Experiments were initiated by the backculturing of SK-N-SH at a concentration of $1.0 \times 10^6$ cells/ml in the appropriate treatment media. Cell density did not influence the response to 3,17β-estradiol or 3,17α-estradiol.

The neuroprotection assay involved continuous exposure of SK-N-SH cells for 48 h to conditions of serum deprivation and to 2 nM concentrations of each test compound. This concentration is at least 10-fold higher than that required for the neuroprotective effects of 3,17β- and 3,17α-estradiol. 3,17,β-estradiol was used as a control. This compound caused a dose-dependent protection of SK-N-SH cells under conditions of serum deprivation with an $ED_{50}$ of 0.13 nM and significant neuroprotection at the 0.2 nM concentration (FIG. 1). This effect was robust with the 2 nM concentration of 3,17β-estradiol showing neuroprotection in 8 separate trials (FIGS. 1 to 4). Neuroprotection was determined by the magnitude of the difference in live cell number in the treated wells versus the cell number in the serum free wells. The statistical analysis was performed on the raw data in each experiment. The significance of differences among groups was determined by one way analysis of variance. Planned comparisons between groups were done using Scheffe's F-test. For all tests, p<0.05 was considered significant. Following the analysis, data were normalized to the % response of the 3,17β-estradiol group for each study using the following calculation:

$$\% \text{ Neuroprotectivity} = \frac{\text{Test cell \# − Serum-Free Cell \#}}{17\beta \, E2 \text{ Cell \# − Serum-Free Cell \#}}.$$

Cell viability was assessed at 48 h of treatment using the Trypan Blue dye-exclusion method. At the appropriate time, cell suspensions were made by decanting media, rinsing each well with 0.2 ml, 0.02% EDTA, and incubating cells with 0.2% ml, 0.02% EDTA at 37° C. for 30 min. Cells were suspended by repeated pipetting of the EDTA over the cells. One hundred ul aliquots from each cell suspension was incubated with 100 ul of 0.4% Trypan Blue stain (Sigma Chemical Co.) for 5 minutes at room temperature. All suspensions were counted on a Neubauer hemacytometer within 15 minutes of addition of Trypan Blue. Two independent counts of live cells were made for each aliquot.

Figure 2:
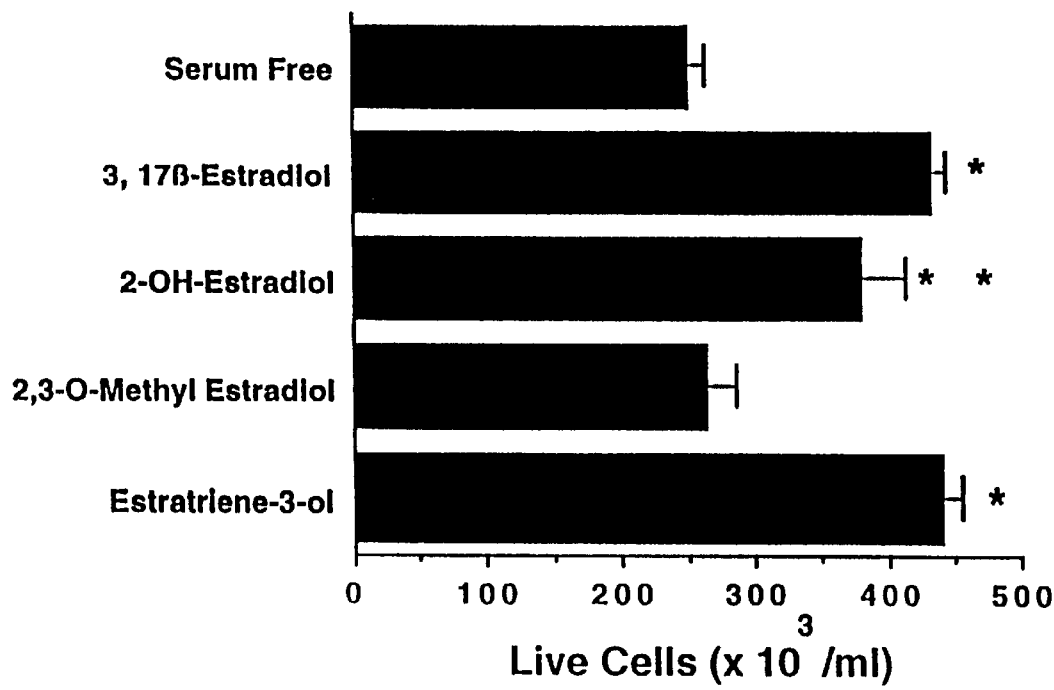
FIG. 2 shows the effects of 3,17β-estradiol, estra-2,3,17 β-triol (2-OH-estradiol), 1,3,5(10)-estratriene-3-ol (estratriene-3-ol) and 2,3-O-methyl estradiol, all at a concentration of 2 nM, on live SK-N-SH cell number at 48 hours of serum deprivation. *=p<0.05 versus serum free controls. **=p<0.05 versus serum free controls and the respective 2,3-O-methyl estradiol. Data are expressed as mean±SEM for 5 wells/group.
Figure 3:
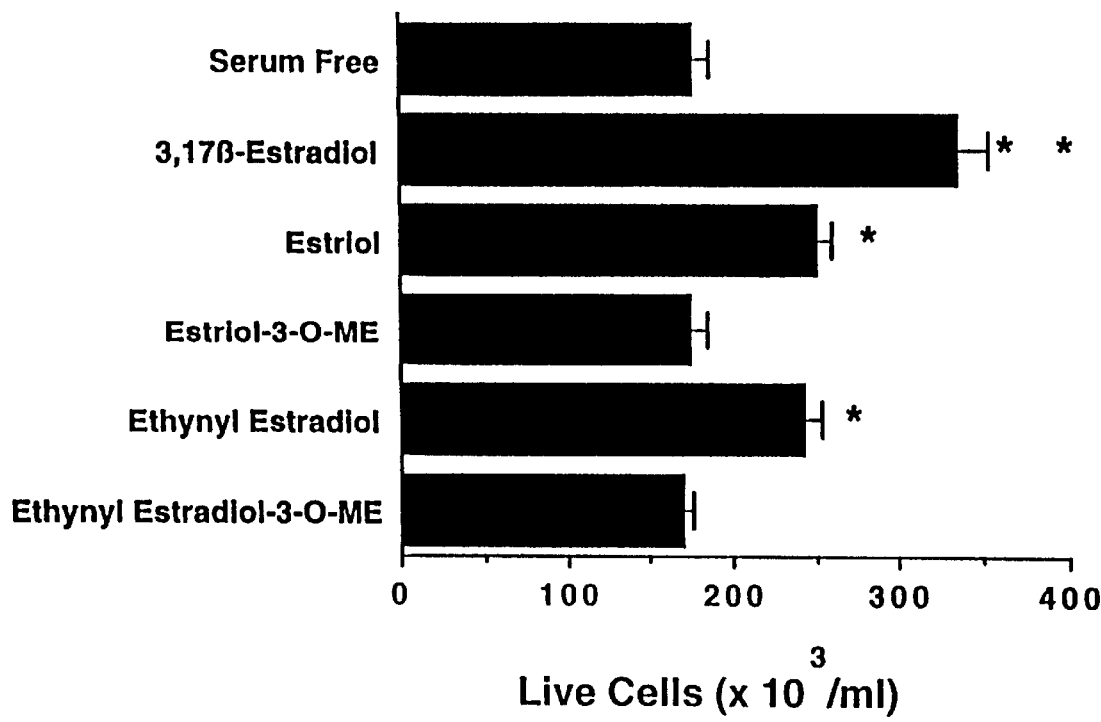
FIG. 3 shows the effects of 3,17β-estradiol, estriol, and 17β ethynyl 3,17β-estradiol (ethynyl estradiol) and their 3-O-methyl ethers; estriol 3-O-methyl ether (estriol 3-O-ME) and ethynyl estradiol 3-O-methyl ether (ethynyl estradiol 3-O-ME), all at a concentration of 2 nM, on live SK-N-SH cell number at 48 hrs of serum deprivation. *-p<0.05 versus serum free controls and the respective 3-O-methyl steroid. **=p<0.05 versus all other groups. Data are expressed as mean±SEM for 5 wells/group.

Example 2: Comparison of the Neuroprotection Afforded by Different Four-Ring and Two-Ring Compositions were found to be equivalent to 3, 17β-estradiol in their neuroprotectivity (FIG. 2, FIG. 13). Estrone, estriol and 17β-ethynyl-3, 17βestradiol, while significantly neuroprotective, were less active than 3,17β-estradiol (FIG. 3 and FIG. 4). The two-ring non-fused diethylstilbestrerol (DES), was active as a neuroprotectant and retained nearly full neuroprotectivity when one, both not both, of the phenolic hydroxyl functions were replaced with an O-methyl ether function (FIG. 4 and FIG. 14). Similarly, all steroids were rendered inactive when the 3-hydroxyl group was replaced with an O-methyl ether group (FIGS. 1–4 and FIGS. 13 and 14), a substitution that eliminates the acid, hydrophilic properties of the A ring. The 3-O methyl ether of 3,17β-estradiol was inactive even at concentrations as high as 20 nM (FIG. 1). These data demonstrate that C-3 hydroxylated estratrienes are neuroprotective. A similarly positioned phenolic hydroxyl group in the diphenols may serve the same function.

Two 19-carbon steroids were evaluated at a 2 nM concentration for neuroprotection in the assay. The following results were obtained for live cells/ml. (mean±SEM×$10^3$/ml) for 5 to 6 cultures/group; Study 1; serum free controls=94±7, testosterone=87±6, dihydrotestosterone=90+7, cholesterol= 65+4; Study 2; serum free controls=177±18,3,17 β-estradiol=329±33(p<0.05 vs serum free controls), prednisolone=187±16,6α-methylprednisolone=173±13, aldosterone=132±18. There was no neuroprotective effects of any non-phenolic steroids.

The two androgens containing a C-3 ketone, namely the partially unsaturated testosterone that lacks a phenolic A ring, and the saturated compound that lacks a phenolic A ring, dihydrotestosterone, were both inactive. Similarly, all five of the 21-carbon pregnane progesterone and aldosterone and two $\Delta^{1,4}$-steroids, prednisolone and 6-methylprednisolone were inactive. Finally, cholesterol was tested because it has a 3-hydroxyl function on a completely saturated A ring and was inactive. The conformational shape of the flat, phenolic ring and/or the enhanced acidity of phenols relative to cyclohexanols may be important in conferring the observed neuroprotective activity.

In all studies, cells were cultured in RPMI-1640 media (Serum Free, SF group), RPMI-1640 media supplemented with 10% FBS (FBS group), or RPMI-1640 media supplemented one of the following steroids at a concentration of 2 nM (unless otherwise noted): 3,17β-estradiol (1,3,5(10)-estratriene-3,17β-diol); 3,17α-estradiol (1,3,5(10)-estratriene-3β,17α-diol); 3,17β-estradiol 3-O-methyl ether (1,3,5(10)-estratriene-3,17β-diol 3-O-methyl ether); 3,17α-estradiol 3 acetate (1,3,5(10)-estratriene-3β,17α-diol 3-acetate); estrone (1,3,5(10)-estratriene-3-ol-17-one); estrone 3-O-methyl ether (1,3,5(10)-estratriene-3-ol-17-one 3-O-methyl ether); estriol (1,3,5(10)estratriene-3β,16α, 17β-triol); estriol3-O-methyl ether (1,3,5(10)estratriene-3β, 16α,17β-triol 3-O-methyl ether); 17α-ethynyl estradiol (1,3, 5(10)-estratriene-17α-ethynyl-3β,17α-diol); ethynyl estradiol 3-O-methyl ether (1,3,5(10)-estratriene-17α-ethynyl-3β,17α-diol 3-O-methyl ether); 2-hydroxyestradiol (1,3,5 (10)estratriene-2, 3,17β-triol); 2,3-methoxyestradiol (1,3,5 (10)estratrien-2,3,17β-triol 2,3-O-methyl ether) or estratriene-3-ol (1,3,5(10)estratrien-3-ol); cortisone, progesterone, prednisolone (1,4-pregnadience-11β,17,21- triol-3,20-dione); methylprednisolone (6α-methyl-1,4-pregnadiene-11β,17,21-triol-3,20-dione); and aldosterone (4-pregnen-11β,21-diol-3,18,20-trione). All steroids were from Steraloids, Inc., Wilton, N.H. and were initially dissolved at 1 mg/ml in absolute ethanol and diluted in RPMI-1640 media to a final concentration of 2 nM. To control for possible ethanol effects in the treated wells, both the serum-free media (SF group) and FBS media (FBS group) were supplemented with absolute ethanol at a concentration of 544 pl/ml. In all studies, at least 4 and usually 6 replicate well were treated with each media.

Example 3: Three Ring Structures With Neuroprotective Properties

Figure 5:
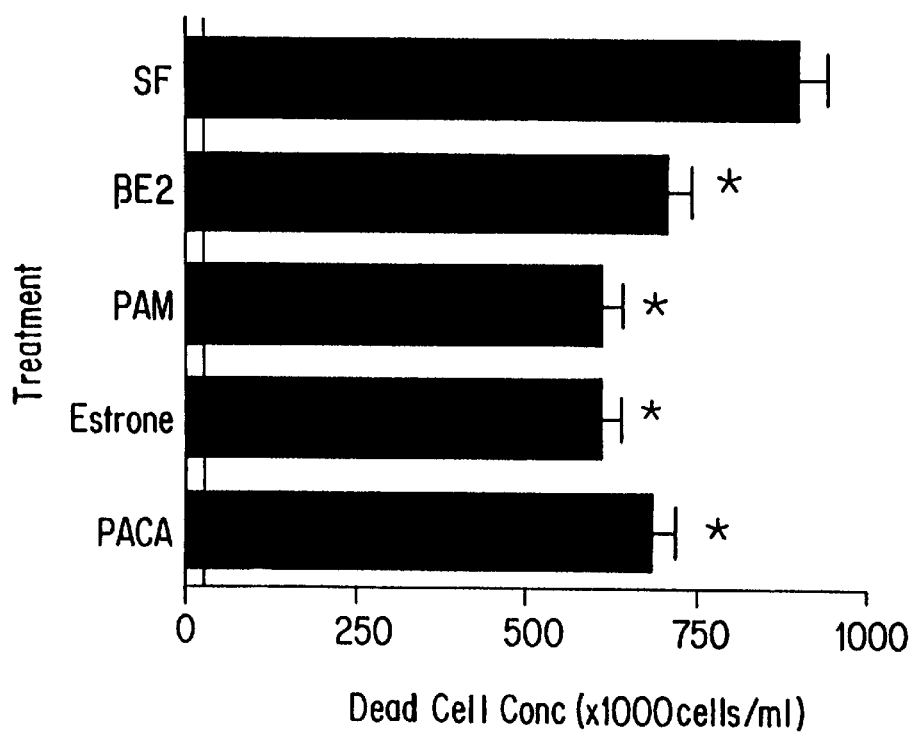
FIG. 5 shows the effects of 3,17β-estradiol, estrone, [2S-(2a,4aβ, 10aβ]-1,2,3,4,4a,9,10,10a-octahydro-7-hydroxy-2-methyl-2-phenanthrenemethanol (PAM), and [2S-(2a,4aα,10aβ]-1,2,3,4,4a, 9,10,10a-octahydro-7-hydroxy-2-methyl-2-phenanthrenecarboxyaldehyde (PACA) at a concentration of 2 nM on SK-N-SH dead cell number at 48 hrs of serum deprivation. *=p,0.05 versus serum free controls (SF). Data are expressed as mean ±SEM for 6 wells/group.
Figure 6:
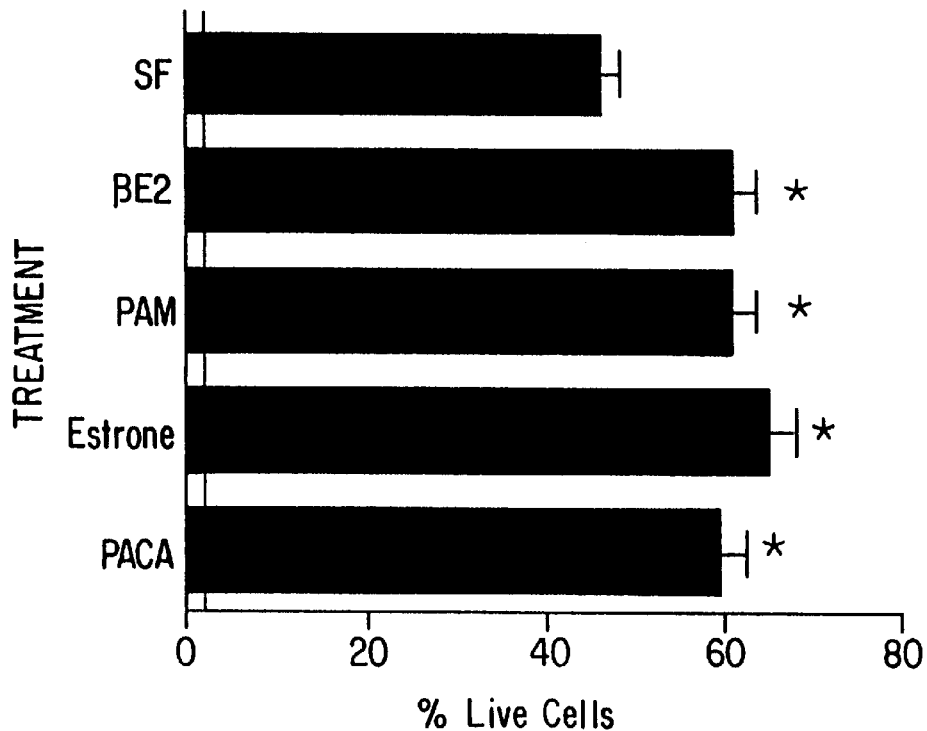
FIG. 6 shows the effects of 3,17β-estradiol, estrone, [2S-(2a,4aα,10aβ]-1,2,3,4,4a,9,10,10a-octahydro-7-hydroxy-2-methyl-2-phenanthrenemethanol (PAM) and [2S-(2a, 4aα, 10aβ]-1,2,3,4,4a,9,10,10a-octahydro-7-hydroxy-2-methyl-2-phenanthrenecarboxyaldehyde (PACA) at 2nM on SK-N-SH live cell number at 48 hrs of serum deprivation. *=p<0.05 versus serum free controls (SF). Data are expressed as mean±SEM for 6 wells/group FIG. 6a shows the effects of [2S-(2a, 4aα,10aβ]-1,2,3,4, 4a,9,10,10a-octahydro-7-hydrosy-2-methyl-2-phenanthrenemethanol (PAM) at 2nM on the percent increase of live cell number over the serum free controls at 48 hrs of serum deprivation. *=p<0.05 versus serum free controls (SF). Statistical analysis was performed on raw data. Data are expressed as mean±SEM for 8 wells/group.
Figure 6A:
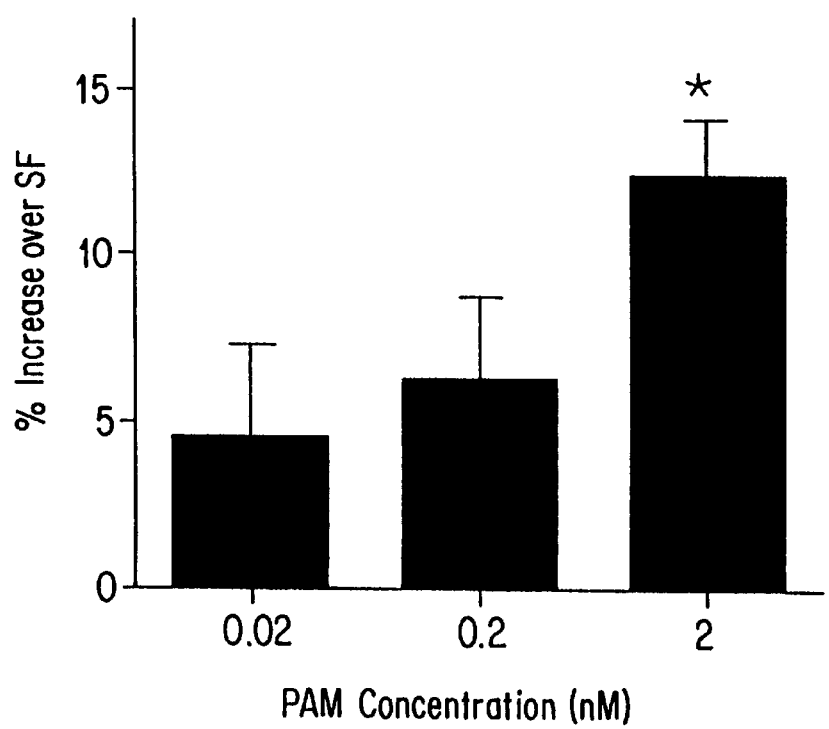
FIG. 6b shows the effects of [2S-(2a ,4a α,10a β]-1,2,3, 4,4a,9,10,10a -octahydro-7-hydroxy-2-methyl-2-phenanthrenecarboxyaldehyde (PACA) on the percent increase of live cell number over the serum free controls at 48 hrs of serum deprivation. *=p<0.05 versus serum free controls (SF). Statistical analysis was performed on raw data. Data are expressed as mean±SEM for 8 wells/group.
Figure 6B:
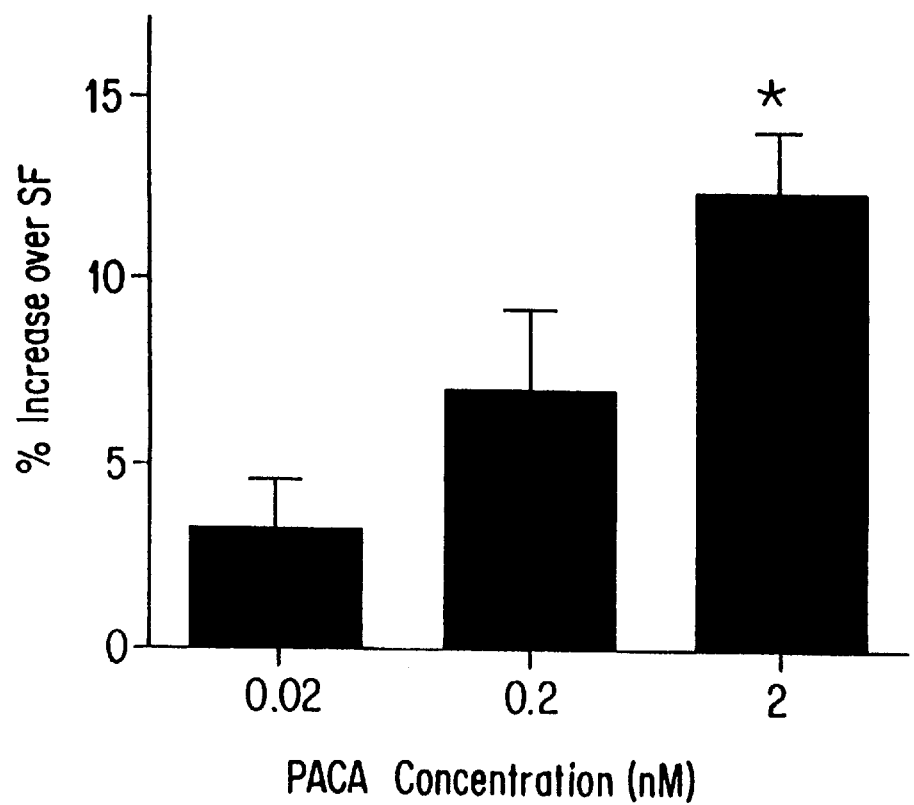
Figure 7:
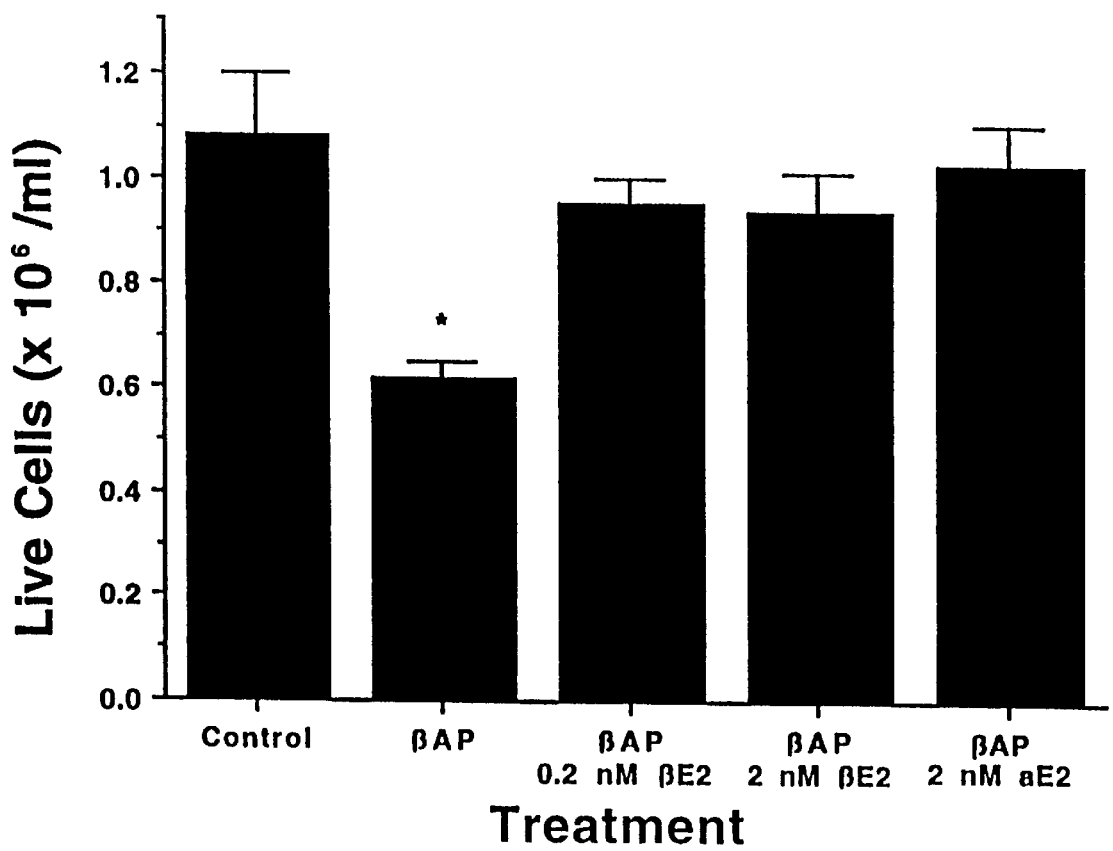
FIG. 7 shows the effects of treatment of 3,17β-estradiol (0.2 or 2 nM) and 3,17α-estradiol (2 nM) on the toxicity induced by the neurotoxic fragment of the β amyloid protein (Aβ25–35) (20 μm) on neuronal cells. SK-N-SH neurons were exposed to 3,17β estradiol, 3,17α-estradiol and Aβ25–35 alone or in combination. After a four-day exposure, live cell number was determined. *=p,0.05 versus serum free controls (SF). Data are expressed as mean±SEM for 6 wells/group. Separate groups were exposed to 3,17β-estradiol and 3,17α-estradiol without the addition of Aβ. The steroid addition had no effect on cell number in the absence of insult.

[2S-(2a ,4aα,10αβ)]-1,2,3,4,4a,9,10, 10a -octaydro-7hydroxy-2-methyl-2-phenanthrenemethanol (PAM) and [2S-(2a , 4aα,10αβ)]-1,2,3,4,4a,9, 10,10a -octaydro-7hydroxy-2-methyl-2-phenanthrenecarboxyaldehyde (PACA) were added to media containing SK-N-SH cells concurrent with serum deprivation. 24 or 48 hrs later, cell viability was determined by a dye production method that required the activity of mitochondria for reduction of the dye to a colored reagent. (Goodwin et al. (1995) J. Immunol. Methods, 179:95). Both PACA and PAM showed neuroprotective activity with peak responses at the 2 nM concentration. (FIGS. 5a, 6a) Neuroprotective activity was similar to the positive control, 3,17 βestradiol. (FIGS. 5 and 6)

Example 4: "In Vivo" Dosage Studies

A number of compounds were tested at doses of 100 ug/kg body weight in rats injected at 2 hrs prior to occlusion of the middle cerebral artery. The injection produced plasma estradiol concentrations of 100 to 200 pg/ml (0.4 to 0.8 nM) at the time of the occlusion. In ovariectomized rats, maximal lesions of 25% of the brain cross-sectional area was observed. When treated with 3,17β-estradiol, maximal lesion area was reduced by about 50%. These data demonstrate that only low nM concentrations of 3,17β estradiol are required to protect from ischemic lesions in vivo.

We claim:

1. A method for conferring neuroprotection on a population of cells in a subject, the method comprising:
   (i) providing a non-estrogen compound having a terminal phenol group in a four-ring cyclopentanophenanthrene structure, the compound having a molecular weight of less than 1000 Daltons; and
   (ii) administering the compound in an effective dose to the population of cells so as to confer neuroprotection.

2. A method according to claim 1, wherein the effective dose achieves a plasma concentration of less than 500 nM.

3. A method according to claim 1, wherein the terminal phenol group has a hydroxyl group on any of carbons 1–4.

4. A method according to claim 2, wherein the effective dose achieves a plasma concentration in the range 0.02 nM–1 nM.

5. A method according to claim 4, wherein the effective dose achieves a plasma concentration in the range 0.1 nM–1 nM.

6. A method according to claim 1, wherein the terminal phenol group is a phenolic A ring.

7. A method of treating a neurodegenerative disease by conferring neuroprotection in a subject, the method comprising:
   (a) preparing an effective dose of a formulation to achieve a plasma concentration of less than 500 nM the formulation containing a non-estrogen compound having a terminal phenol in a four-ring cyclopentanophenanthrene structure, the compound having a molecular weight less than 1000 Daltons; and
   (b) administering the dose to the subject.

8. A method according to claim 7, wherein the terminal phenol is a phenolic A ring.

* * * * *

UNITED STATES PATENT AND TRADEMARK OFFICE
CERTIFICATE OF CORRECTION

PATENT NO. : 5,859,001
DATED      : January 12, 1999
INVENTOR(S): Gordon et al.

It is certified that error appears in the above-identified patent and that said Letters Patent is hereby corrected as shown below:

Column 1; line 5: Please insert --This patent was created with support from the National Institute on Aging under grant number AG-10485, and the U.S. Government has certain rights to the invention.--

Signed and Sealed this

Second Day of May, 2000

*Attest:*

Q. TODD DICKINSON

*Attesting Officer*   Director of Patents and Trademarks